United States Patent
Luo et al.

(10) Patent No.: US 8,088,952 B2
(45) Date of Patent: Jan. 3, 2012

(54) IONIC BRONSTED ACID

(75) Inventors: Lubin Luo, Baton Rouge, LA (US);
Zhike Wang, Baton Rouge, LA (US);
Steven P. Diefenbach, Baton Rouge, LA (US); Xiao Wu, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 404 days.

(21) Appl. No.: 12/374,411

(22) PCT Filed: Jul. 2, 2007

(86) PCT No.: PCT/US2007/072642
§ 371 (c)(1),
(2), (4) Date: Jan. 20, 2009

(87) PCT Pub. No.: WO2008/011266
PCT Pub. Date: Jan. 24, 2008

(65) Prior Publication Data
US 2009/0326273 A1   Dec. 31, 2009

Related U.S. Application Data

(60) Provisional application No. 60/831,377, filed on Jul. 17, 2006.

(51) Int. Cl.
*C07C 211/00* (2006.01)
(52) U.S. Cl. ........ 564/442
(58) Field of Classification Search .......... None
See application file for complete search history.

(56) References Cited

U.S. PATENT DOCUMENTS

| 7,897,707 B2 * | 3/2011 | Luo et al. .......... 526/141 |
| 7,902,390 B2 * | 3/2011 | Wang et al. ........ 556/179 |
| 2002/0132945 A1 | 9/2002 | Wu et al. |

FOREIGN PATENT DOCUMENTS

EP    1 113 026 A2    7/2001

\* cited by examiner

*Primary Examiner* — Sudhakar Katakam
(74) *Attorney, Agent, or Firm* — James A. Jubinsky

(57) ABSTRACT

A new ionic compound is provided that is derived from N,N-dimethylaniline and pentafluorophenol in amounts such that there are at least 2 equivalents of pentafluorophenol per equivalent of the N,N-dimethylaniline.

3 Claims, 3 Drawing Sheets

Figure 1 Proton NMR Spectrum

IONIC BRONSTED ACID

BACKGROUND

Partially hydrolyzed aluminum alkyl compounds known as aluminoxanes (AO) are used for activating transition metals for olefin polymerization activity. One such compound, methylaluminoxane (MAO), is a frequently chosen aluminum co-catalyst/activator in the industry. Considerable effort has been devoted to improving the effectiveness of catalyst systems based on use of aluminoxanes or modified aluminoxanes for polymerization of olefins. Representative patents and publications in the field of aluminoxane usage include the following: U.S. Pat. No. 5,324,800 to Welborn et al.; U.S. Pat. No. 4,752,597 to Turner; U.S. Pat. Nos. 4,960,878 and 5,041,584 to Crapo et al.; WO 96102580 to Dail'occo, et al.; EP 0 277 003 and EP 0 277 004 to Turner; Hlalky, Turner, and Eckman, *J. Am. Chem. Soc.*, 1989, 111, 2728-2729; Hialky and Upton, *Macromolecules*, 1996, 29, 8019-8020. U.S. Pat. No. 5,153,157 to Hiatky and Turner; U.S. Pat. No. 5,198,401 to Turner, Hialky, and Eckman; Brintzinger, et al., *Angew, Chem. Int. Ed, Engl.*, 1995, 34, 1143-1170; and the like. Despite technological advances, many aluminoxane-based polymerization catalyst activators still lack the activity and/or thermal stability needed for commercial applicability, require commercially unacceptably high aluminum loading, are expensive (especially MAO), and have other impediments to commercial implementation.

Many of the limiting features surrounding the use of aluminoxanes as activators for transition metals, for example, activity limitations—and the need for high aluminum loading, can be addressed by the use of stable or metastable hydroxyaluminoxanes. As compared to aluminoxanes, hydroxyaluminoxanes are generally highly active, provide reduced levels of ash, and result in improved clarity in polymers formed from such catalyst compositions. One representative hydroxyaluminoxane is hydroxyisobutylaluminoxane (HO-IBAO), which can be derived from the low-temperature hydrolysis of triisobutylaluminum (TIBA), Hydroxyaluminoxane compositions are disclosed in U.S. Pat. Nos. 6,562,991, 6,555,494, 6,492,292, 6,462,212, and 6,160,145.

In contrast to aluminoxanes, which appear to act as Lewis acids to activate transition metals, hydroxyaluminoxane species (generally abbreviated HO—AO) comprise active protons, and appear to activate transition metals by functioning as Bronsted acids. As used herein, an active proton is a proton capable of metal alkyl protonation. A typical hydroxyaluminoxane comprises a hydroxyl group bonded to at least one of its aluminum atoms. To form hydroxyaluminoxanes, typically a sufficient amount of water is reacted with an alkyl aluminum compound under appropriate conditions, for example at low temperature in hydrocarbon solvents, such that a compound having at least one HO—Al group is generated, which is capable of protonating a hydrocarbyl ligand from a d- or f-block organometallic compound to form a hydrocarbon. Therefore, polymerization catalysts derived from a hydroxyaluminoxane usually comprise: 1) a cation derived from a transition, lanthanide or actinide metal compound, for example a metallocene, by loss of a leaving group, and 2) an aluminoxate anion derived by transfer of a proton from a stable or metastable hydroxyaluminoxane to the leaving group. The leaving group is usually transformed into a neutral hydrocarbon thus rendering the catalyst-forming reaction irreversible.

One feature of hydroxyaluminoxanes is that their active protons are often thermally unstable when maintained in solution at ambient temperatures, likely due to the loss of active protons through alkane elimination. Thus, hydroxyaluminoxanes are frequently stored at temperatures lower than ambient temperature to maintain the active proton concentration. Typical low temperature storage is from about −20° C. to about 0° C. in the absence of such low temperature handling, the hydroxyaluminoxane activity decreases rapidly. Low-temperature storage is commercially cost prohibitive, especially over extended periods of time.

Thus, a need exists for hydroxyaluminoxane-type compositions that have more thermally-robust active protons, as compared to currently available hydroxyaluminoxanes, and that exhibit suitably high activity for commercial olefin polymerization.

THE INVENTION

This invention provides

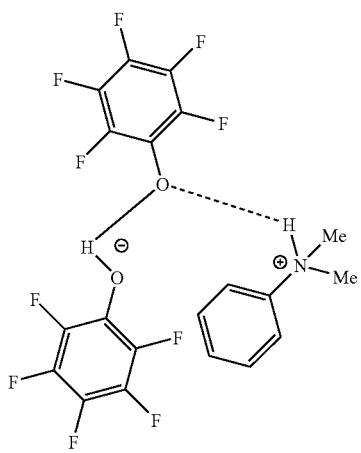

([HNPhMe$_2$]$^+$[H(OC$_6$F$_5$)$_2$]$^-$). This invention also provides compounds derived from at least N,N-dimethylaniline and pentafluorophenol in amounts such that there are at least two equivalents of pentafluorophenol per equivalent of the N,N-dimethylaniline. This invention also provides methods of making an ionic compound comprising combining at least N,N-dimethylaniline and pentafluorophenol in amounts such that there are at least two equivalents of pentafluorophenol per equivalent of the N,N-dimethylaniline. Use of the term "at least" indicates that other components may possibly be included when combining the N,N-dimethylamine and pentafluorophenol in amounts such that there are at least two equivalents of pentafluorophenol per equivalent of the N,N-dimethylaniline, or deriving a compound therefrom. For example, a compound of this invention could be derived from, or made from a method comprising combining, (i) N,N-dimethylaniline and pentafluorophenol in amounts such that there are at least two equivalents of pentafluorophenol per equivalent of this N,N-dimethylaniline, and (ii) additional N,N-dimethylaniline. This invention also provides a compound comprising N,N-dimethylaniline and two equivalents of pentafluorophenol per equivalent of the N,N-dimethylaniline.

An ionic compound according to this invention has at least one active proton and, thus, is an ionic Bronsted acid. An ionic compound according to this invention is useful in forming activator compositions derived from at least: a) carrier; b) organoaluminoxy compound; and (c) ionic compound having at least one active proton. Such activator compositions are hydroxyaluminoxane type Bronsted acid activators. Ionic compounds of this invention have numerous other uses in industry as wil be apparent to those skilled in the art.

This invention also provides

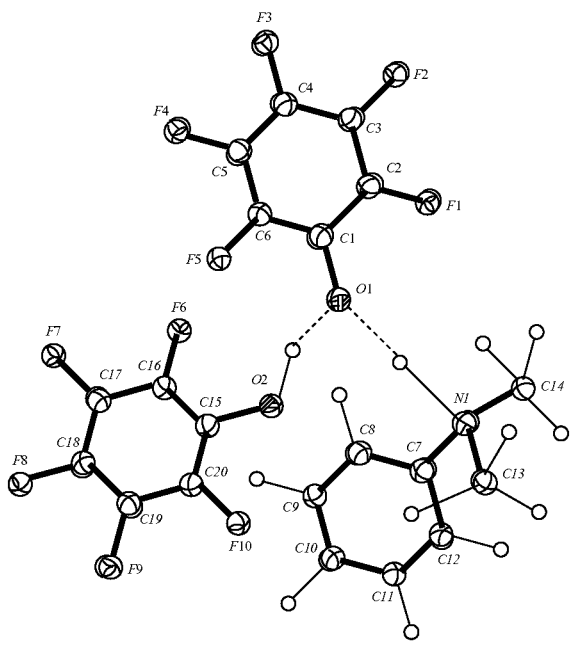

The invention will be better understood by referring to the attached drawings and Appendix in which.

Figure 3:
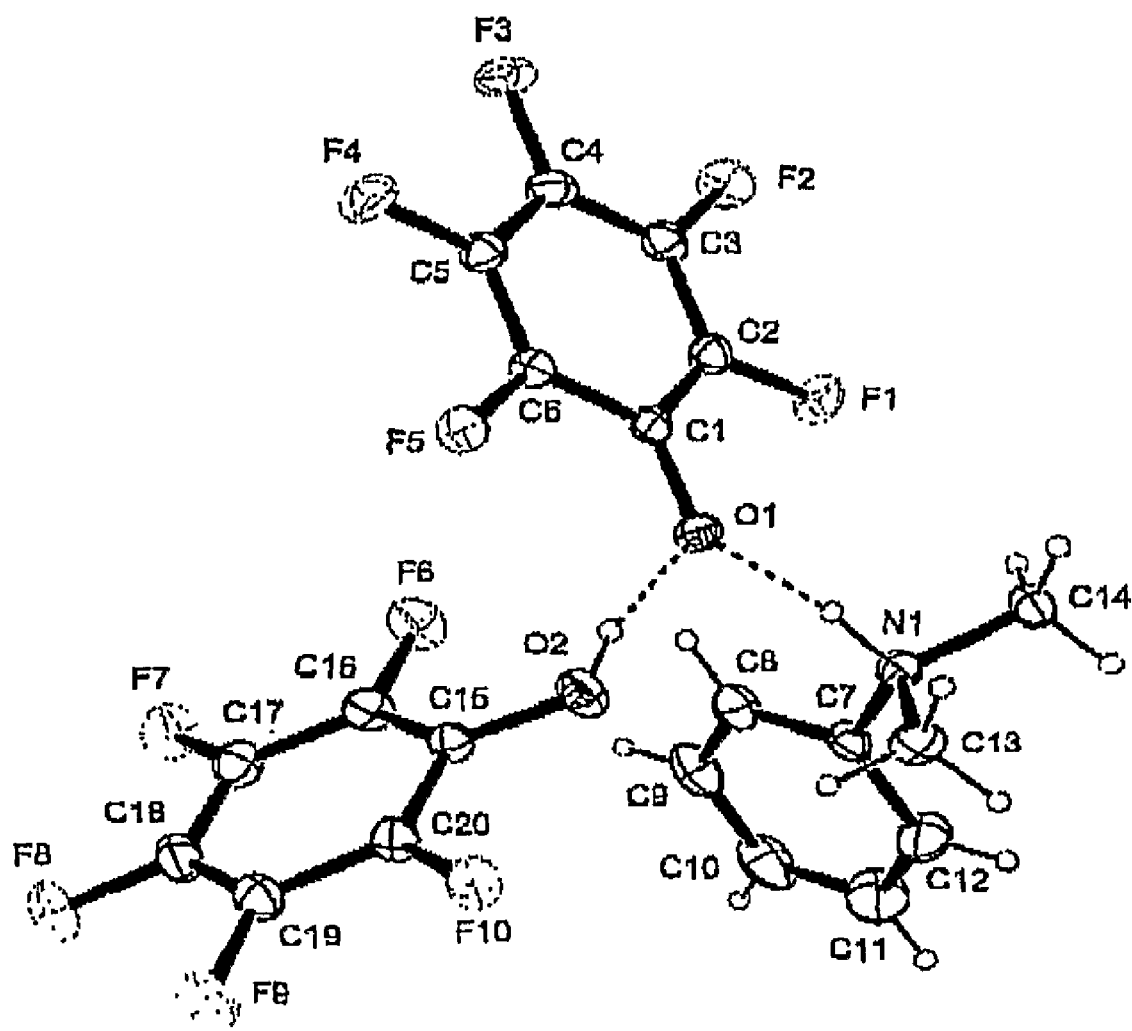

FIG. 3 illustrates an X-ray single-crystal diffraction structure ORTEP Plot of an ionic compound of this invention; and Appendix 1 provides the summary of the instrument information, the crystal data, and the method of the single-crystal X-ray diffraction analysis for the determination of the crystal structure shown in FIG. 3 and the obtained bond parameters, which are listed in the tables in Appendix 1.

Figure 1:
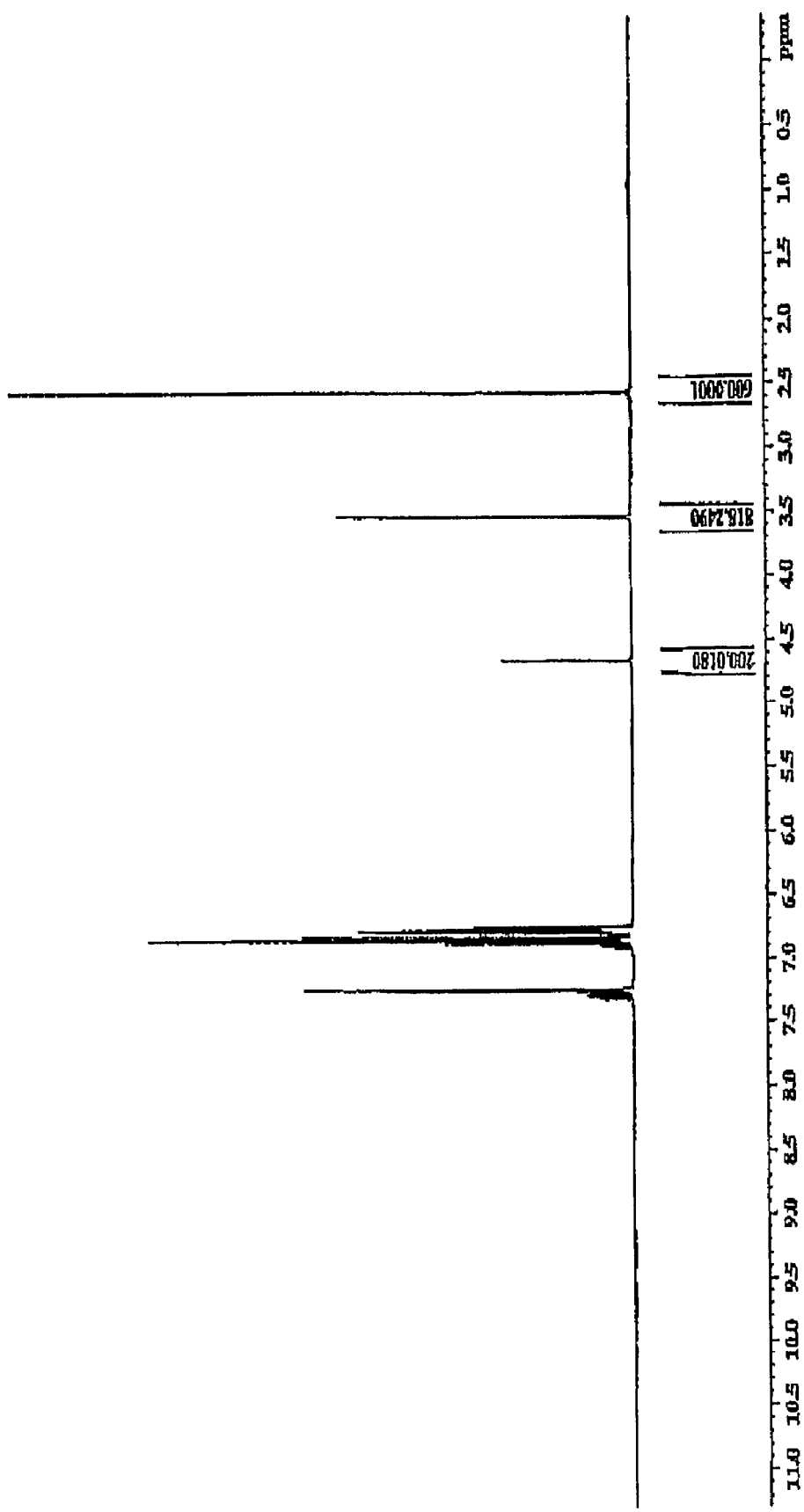
FIG. 1 illustrates a $^1$H (proton) NMR spectrum of an ionic compound of this invention.
Figure 2:
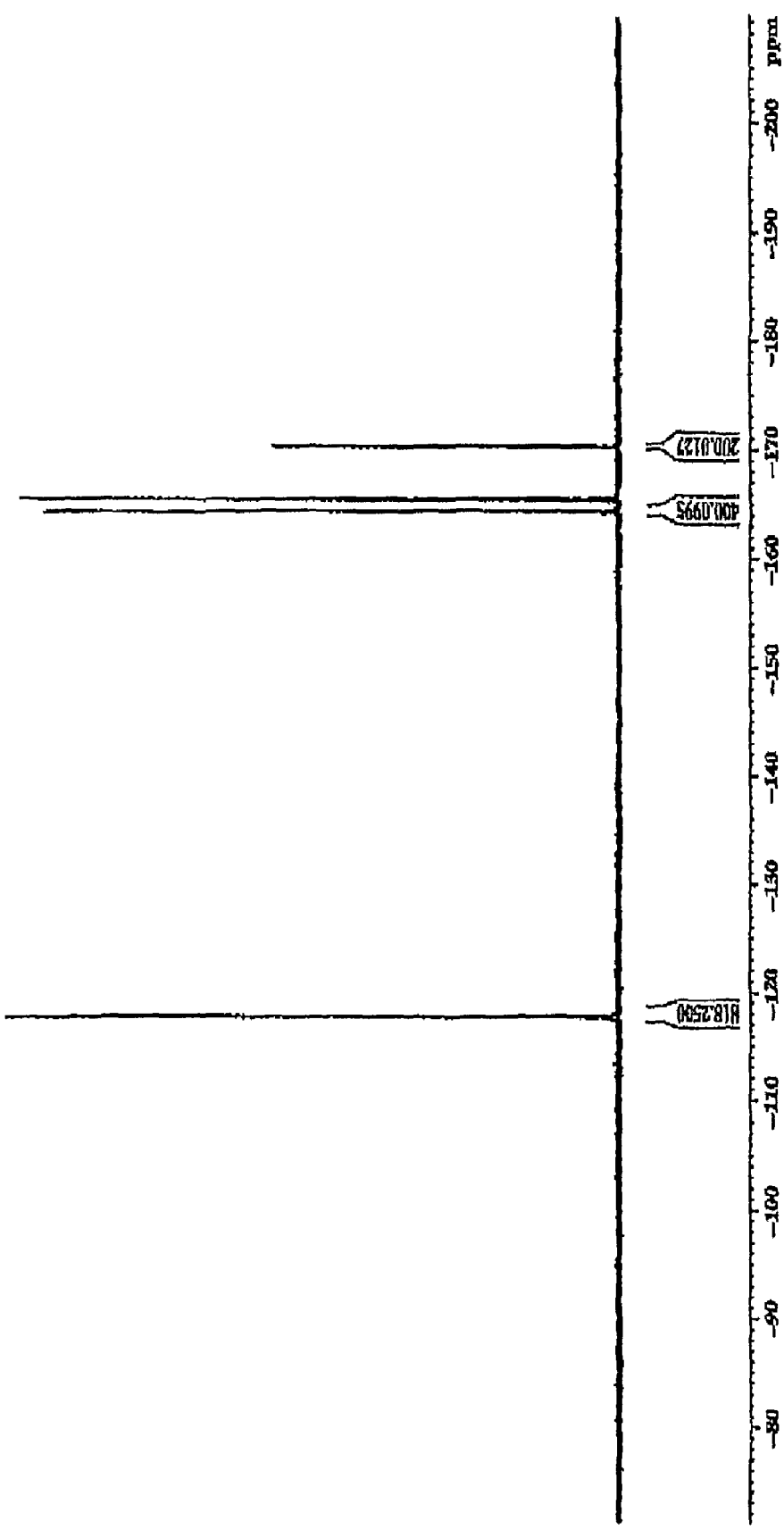
FIG. 2 illustrates a $^{19}$F (fluorine) NMR spectrum of an ionic compound of this invention.

In the spectrum of FIG. 1, $^1$H NMR (400 MHz, 21° C., $C_6D_6$): the singlet peak at 2.5 ppm is —N(CH$_3$)$_2$ (6 protons); the singlet peak at 4.5 ppm is the active proton signal of N—H and O—H (2 protons); the singlet peak at 3.5 ppm is the internal cross-reference compound (4-FC$_6$H$_4$)$_2$CH$_2$ (2 protons for which the integral is set as 818.25 for both proton and fluorine NMR spectra shown in FIG. 1 and FIG. 2); multiple peaks between 6.5 and 7.5 ppm are the aromatic proton signals from N,N'-dimethylaniline and the internal cross-reference compound.

In the spectrum of FIG. 2. $^{19}$F NMR (400 MHz, 21° C., $C_6D_6$): The peak at −170 ppm is the p-F on two $C_6F_5O$— groups (2 F); The two peaks at −165 ppm are the o- and m-F on two C6F5O— groups (4 F for each); The peak near −120 ppm is the p-F on the internal cross-reference compound (p-FC$_6$H$_4$)$_2$CH$_2$ (or (4-FC6H4)$_2$CH$_2$) and its integral is set to 818.25.

Function of the internal cross-reference (ICR) compound: To verify the composition of the IBA compound by NMR, an ICR compound (e.g., p-FC$_6$H$_4$)$_2$CH$_2$ was used as a dual reference for both proton NMR spectrum and fluorine spectrum since the $C_6F_5O$— group on the IBA compound doesn't show any proton signal in proton NMR, whereas the PhNMe$_2$ group on the IBA compound doesn't show any fluorine signal in fluorine NMR. (p-FC$_6$H$_4$)$_2$CH$_2$ shows both proton and fluorine NMR signals as two p-F at about −120 ppm and two protons at 3.5 ppm. Once the integrals of these two NMR peaks are set to the same value, the ratio of $C_6F_5O$— to PhNMe$_2$ can be calculated. The current NMR data show that the ratio of $C_6F_5O$— to PhNMe$_2$ is 2:1. Of course the proton NMR showing an active proton peak at 4.5 ppm with an integral of 200, which is from the $C_6F_5$OH, is also a confirmation of the 2:1 ratio of $C_6F_5O$— to PhNMe$_2$.

In the ORTEP Plot of the IBA Single-Crystal Structure of FIG. 3, the small circle o represents a proton.

Ionic Compound Having at Least One Active Proton

This invention provides ionic compound having at least one active proton derived from at least N,N-dimethylaniline and 2 equivalents (e.g., moles) of pentafluorophenol per equivalent (e.g., mole) of the N,N-dimethylaniline. Ionic compound having at least one active proton

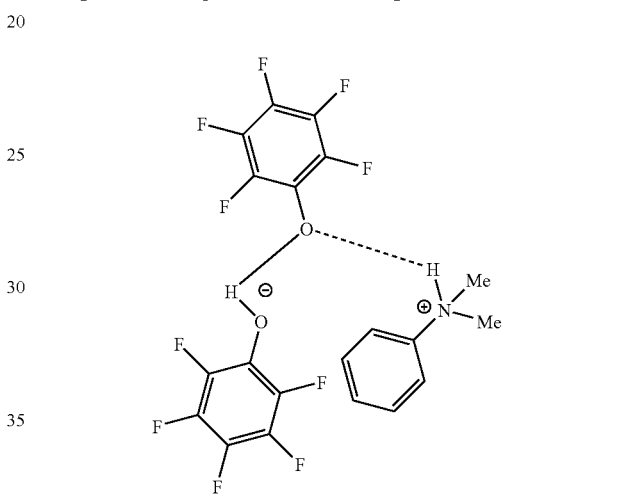

can be derived according to the following reaction:

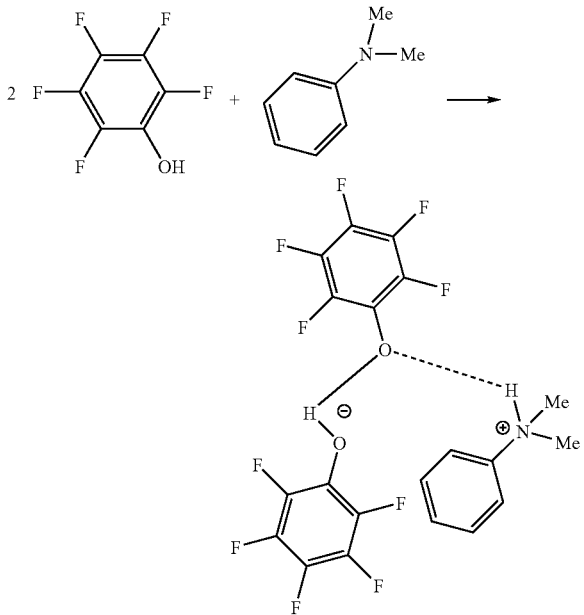

Use of Ionic Compound of this Invention in Activator Composition/Catalyst

An activator composition that uses an ionic compound of this invention can comprise a carrier, an organoaluminoxy compound, and an ionic compound having at least one active proton. Such an activator composition is useful in catalysts for olefin polymerization.

The carrier, the organoaluminoxy compound, and the ionic compound having at least one active proton can be combined in an inert gas atmosphere; at a temperature of about −80° C. to about 200° C., and at a combining time of about 1 minute to about 36 hours. Aliphatic solvent or aromatic solvent may be used, either of which is inert to the carrier, the organoaluminoxy compound, and the ionic compound having at least one active proton. Example treatments after completion of the combining operation include filtration of supernatant, followed by washing with inert solvent and evaporation of solvent under reduced pressure or in inert gas flow, but these treatments are not required. The resulting activator composition can be used for polymerization in any suitable state, including fluid, dry, or semi-dry powder, and may be used for polymerization in the state of being suspended in inert solvent, Catalyst for Olefin Polymerization The activator composition derived from at least the ionic compound of this invention and a suitable transition metal component, as will be familiar to those skilled in the art, can each be added independently, yet substantially simultaneously, to monomer to catalyze polymerization. The activator composition and suitable transition metal component can be combined to form product and at least a portion of the product can be added to monomer to catalyze polymerization

EXAMPLES

Syntheses of Ionic Compound Having at Least One Active Proton

Example 1

An ionic compound was synthesized from 2 moles of pentafluorophenol per mole of N,N-dimethylaniline, isolated as a solid crystalline material, and characterized. In a drybox, 0.1892 grams of $C_6F_5OH$ (pentafluorophenol) was dissolved in about 2 grams of dry isohexane in a flask to make solution A. 0.1249 grams of $NMe_2$ Ph (N,N-dimethylaniline) was put into a vial, then about 1 gram of dry isohexane was added to make solution B. Solution B was transferred into solution A with a pipette. In about 1-2 minutes, some crystalline solid formed. The solid was washed with isohexane twice and then dried under vacuum. The resulting solid was analyzed by both H- and F-19 NMR using 4,4-difluorophenylmethane as a cross reference. The results indicated that the solid had a composition of two moles of pentafluorophenol per mole of N,N-dimethylaniline. The crystalline solid was also analyzed with X-ray single-crystal diffraction method to obtain the crystal structure (see FIG. 3 and Appendix 1).

Example 2

In a drybox, 2.00 g (0.0108 mol) of $C_6F_5OH$ (pentafluorophenol) was mixed with 0.657 g (0.00540 mol) of $NMe_2$ Ph (N,N-dimethylaniline) in a vial. After a few hours the slurry mixture solidified to form a crystalline solid. The resulting solid was analyzed by H-NMR; the analysis confirmed a composition of two moles of pentafluorophenol per mole of N,N-dimethylaniline.

The results of conductivity tests of samples prepared with pentafluorophenol and/or N,N-dimethylaniline in acetonitrile are shown in Table 1, Sample No. 3 was prepared from mixture of 2.00 g (0.0108 mol) of $C_6F_5OH$ (pentafluorophenol) and 1.31 g (0.0108 mol) of $NMe_2$ Ph (N,N-dimethylaniline). Sample No. 4 was prepared according to the procedures given in Example 2.

TABLE 1

Conductivity Results Obtained in $CH_3CN$ Solution at Room Temperature

| | Sample No. | | | |
|---|---|---|---|---|
| | 1 | 2 | 3 | 4 |
| Sample | $C_6F_5OH$ only | $PhNMe_2$ only | $C_6F_5OH$ + $PhNMe_2$ (1:1) | $C_6F_5OH$ + 0.5 $PhNMe_2$ (2:1) |
| Concentration (mmol/g) of phenol | 1.09 | 1.09[1] | 1.09 | 1.09 |
| Conductivity (uS/cm) | 314 | 92.9 | 2,217 | 2,049 |

[1]concentration of amine (since no phenol included)

The increase in conductivity of samples 3 and 4 (over that of samples 1 and 2) confirms the formation of ionic species. In sample 3, the excess amine adds to the conductivity, but not substantially. The excess amount of amine in the 1:1 charged sample (sample 3) does not form significantly more ionic compound. Therefore, a 1:1 charge of the two components only forms 0.5 equivalent of the ionic species with 0.5 equivalent of excess amine.

Therefore, we have confirmed that either in solution state (through NMR and conductivity analyses) or in solid state (through X-ray single crystal diffraction analysis), the IBA compound has a composition of two equivalents of $C_6F_5OH$ and one equivalent of $PhNMe_2$.

While the present invention has been described in terms of one or more preferred embodiments, it is to be understood that other modifications may be made without departing from the scope of the invention, which is set forth in the claims below.

APPENDIX 1

| Experimental | |
|---|---|
| Crystal data | |
| $C_6HF_5O \cdot C_6H_{12}N^+ \cdot C_6F_5O^-$ | Mo Kα radiation |
| $M_r = 489.31$ | $\lambda = 0.71073$ Å |
| Monoclinic | Cell parameters from 7920 reflections |
| $P2_1/c$ | $\theta = 2.5$-$33.7°$ |
| $a = 11.4627 (11)$ Å | $\mu = 0.170$ mm$^{-1}$ |
| $b = 10.5885 (10)$ Å | $T = 110$ K |
| $c = 17.1863 (13)$ Å | Prism |
| $\beta = 109.377 (4)°$ | Colorless |
| $V = 1968.0 (3)$ Å$^3$ | $0.40 \times 0.35 \times 0.23$ mm |
| $Z = 4$ | Crystal source local laboratory |
| $D_r = 1.651$ Mg m$^{-3}$ | |
| $D_m$ not measured | |
| Data collection | |
| KappaCCD (with Oxford Cryostream) diffractometer | 6193 reflections with $I > 2\sigma(I)$ |
| $\omega$ scans with $\kappa$ offsets | $R_{int} = 0.019$ |
| Absorption correction zone | $\theta_{max} = 33.7°$ |
| 64619 measured reflections | $h = -17 \rightarrow 17$ |
| 7767 independent reflections | $k = -16 \rightarrow 16$ |
| | $l = -26 \rightarrow 26$ |
| | intensity decay <1% |

APPENDIX 1-continued

Experimental

Refinement

| Refinement on $F^2$ | $w = 1/[\sigma^2(F_o^2) + (0.0466P)^2 + 0.5472P]$ where $P = (F_o^2 + 2F_c^2)/3$ |
|---|---|
| $R[F^2 > 2\sigma(F^2)] = 0.038$ | |
| $\omega R(F^2) = 0.106$ | $(\Delta/\sigma)_{max} = 0.001$ |
| $S = 1.064$ | $\Delta\rho_{max} = 0.49$ e Å$^{-1}$ |
| 7767 reflections | $\Delta\rho_{min} = -0.23$ e Å$^{-3}$ |
| 307 parameters | Extinction correction: SHELXL |
| H atoms treated by a mixture of independent and constrained refinement | Extinction coefficient: 0.0030 (9) Scattering factors from International Tables for Crystallography (Vol. C) |

TABLE 1

Fractional atomic coordinates and equivalent isotropic displacement parameters (Å$^2$)
$U_{eq} = (1/3)\Sigma_i\Sigma_j U^{ij}a^i a^2 a_i, a_2.$

| | x | y | z | $U_{eq}$ |
|---|---|---|---|---|
| F1 | 0.85155 (7) | 0.45284 (6) | 0.30159 (4) | 0.02916 (14) |
| F2 | 0.85027 (7) | 0.70714 (6) | 0.31625 (4) | 0.03202 (15) |
| F3 | 0.84617 (7) | 0.81265 (6) | 0.46906 (4) | 0.03134 (15) |
| F4 | 0.84331 (7) | 0.65913 (6) | 0.58935 (4) | 0.02916 (14) |
| F5 | 0.84571 (6) | 0.40638 (6) | 0.57392 (3) | 0.02378 (12) |
| O1 | 0.84986 (6) | 0.29628 (6) | 0.42904 (4) | 0.01966 (13) |
| N1 | 0.85427 (7) | 0.14259 (7) | 0.31054 (5) | 0.01788 (14) |
| H1N | 0.8476 (12) | 0.2094 (12) | 0.3438 (8) | 0.021 |
| C1 | 0.84675 (8) | 0.41915 (6) | 0.43646 (5) | 0.01620 (15) |
| C2 | 0.84765 (8) | 0.50280 (9) | 0.37313 (5) | 0.01877 (16) |
| C3 | 0.84755 (9) | 0.63271 (9) | 0.38120 (6) | 0.02113 (17) |
| C4 | 0.84508 (9) | 0.68663 (9) | 0.46378 (6) | 0.02140 (17) |
| C5 | 0.84346 (8) | 0.60840 (9) | 0.51774 (6) | 0.01953 (16) |
| C6 | 0.84411 (8) | 0.47866 (9) | 0.50903 (5) | 0.01695 (16) |
| C7 | 0.72908 (8) | 0.10753 (9) | 0.25665 (6) | 0.02031 (16) |
| C8 | 0.03112 (9) | 0.18528 (10) | 0.25454 (6) | 0.02380 (16) |
| H8 | 0.6440 | 0.2690 | 0.2878 | 0.029 |
| C9 | 0.51284 (10) | 0.15311 (13) | 0.20245 (7) | 0.0311 (2) |
| H9 | 0.4444 | 0.2054 | ⅓ | 0.037 |
| C10 | 0.49505 (11) | 0.04549 (15) | 0.15448 (8) | 0.0383 (3) |

TABLE 1-continued

Fractional atomic coordinates and equivalent isotropic displacement parameters (Å$^2$)
$U_{eq} = (1/3)\Sigma_i\Sigma_j U^{ij}a^i a^2 a_i, a_2.$

| | x | y | z | $U_{eq}$ |
|---|---|---|---|---|
| H10 | 0.4144 | 0.0241 | 0.1192 | 0.046 |
| C11 | 0.59435 (12) | −0.03146 (15) | 0.15756 (9) | 0.0444 (3) |
| H11 | 0.5815 | −0.1054 | 0.1245 | 0.063 |
| C12 | 0.71283 (11) | −0.00051 (12) | 0.20904 (8) | 0.0339 (2) |
| H12 | 0.7813 | −0.0527 | 0.2114 | 0.041 |
| C13 | 0.01473 (10) | 0.04004 (9) | 0.37051 (6) | 0.02492 (10) |
| H13A | 0.8596 | 0.0142 | 0.4607 | 0.037 |
| H13B | 0.9926 | 0.0715 | 0.4096 | 0.037 |
| H13C | 0.9315 | −0.0326 | 0.3405 | 0.037 |
| C14 | 0.93410 (9) | 0.18301 (10) | 0.26166 (6) | 0.02162 (17) |
| H14A | 0.9515 | 0.1101 | 0.2321 | 0.032 |
| H14B | 1.0120 | 0.2173 | 0.2990 | 0.032 |
| H14C | 0.8912 | 0.2481 | 0.2219 | 0.032 |
| O2 | 0.82704 (6) | 0.13286 (7) | 0.53190 (6) | 0.02315 (14) |
| H2O | 0.8285 (14) | 0.1973 (15) | 0.4997 (10) | 0.035 |
| F6 | 0.61668 (6) | 0.28956 (6) | 0.46696 (6) | 0.02967 (14) |
| F7 | 0.41282 (6) | 0.24789 (7) | 0.50761 (4) | 0.03272 (15) |
| F8 | 0.40694 (6) | 0.05744 (8) | 0.61355 (5) | 0.03620 (17) |
| F9 | 0.60919 (7) | −0.09634 (7) | 0.67337 (5) | 0.03789 (17) |
| F10 | 0.81278 (6) | −0.05565 (6) | 0.63312 (4) | 0.02774 (14) |
| C15 | 0.72318 (8) | 0.11993 (8) | 0.55008 (6) | 0.01850 (16) |
| C16 | 0.61796 (9) | 0.19536 (9) | 0.51958 (6) | 0.02091 (17) |
| C17 | 0.51260 (9) | 0.17455 (10) | 0.54045 (6) | 0.02319 (18) |
| C18 | 0.50865 (9) | 0.07786 (10) | 0.59316 (6) | 0.02446 (18) |
| C19 | 0.61138 (10) | 0.00081 (10) | 0.62421 (6) | 0.02428 (18) |
| C20 | 0.71584 (9) | 0.02218 (9) | 0.60283 (6) | 0.02030 (17) |

TABLE 2

Hydrogen bonding geometry (Å, °)

| D-H...A | D-H | H...A | D...A | D-H...A |
|---|---|---|---|---|
| N1—H1N...O1 | 0.926 (13) | 1.723 (13) | 2.6207 (10) | 161.6 (12) |
| O2—H2O...O1 | 0.882 (16) | 1.683 (16) | 2.5485 (10) | 166.5 (15) |

TABLE 4

Antsotropic displacement parameters (Å$^2$)

| | $U_{11}$ | $U_{22}$ | $U_{33}$ | $U_{12}$ | $U_{13}$ | $U_{23}$ |
|---|---|---|---|---|---|---|
| F1 | 0.0462 (4) | 0.0262 (3) | 0.0199 (3) | 0.0032 (3) | 0.0173 (3) | 0.0016 (2) |
| F2 | 0.0466 (4) | 0.0234 (3) | 0.0309 (3) | 0.0026 (3) | 0.0195 (3) | 0.0109 (2) |
| F3 | 0.0411 (4) | 0.0149 (3) | 0.0390 (4) | −0.0012 (2) | 0.0146 (3) | −0.0010 (2) |
| F4 | 0.0404 (4) | 0.0246 (3) | 0.0230 (3) | −0.0012 (3) | 0.0112 (3) | −0.0079 (2) |
| F5 | 0.0337 (3) | 0.0226 (3) | 0.0159 (2) | −0.0006 (2) | 0.0094 (2) | 0.0025 (2) |
| O1 | 0.0267 (3) | 0.0154 (3) | 0.0180 (3) | −0.0004 (2) | 0.0088 (2) | −0.0003 (2) |
| N1 | 0.0186 (3) | 0.0185 (3) | 0.0164 (3) | −0.0010 (3) | 0.0057 (3) | −0.0013 (3) |
| C1 | 0.0149 (3) | 0.0171 (3) | 0.0161 (4) | −0.0006 (3) | 0.0045 (3) | 0.0007 (3) |
| C2 | 0.0210 (4) | 0.0193 (4) | 0.0173 (4) | 0.0006 (3) | 0.0081 (3) | 0.0013 (3) |
| C3 | 0.0223 (4) | 0.0191 (4) | 0.0227 (4) | 0.0001 (3) | 0.0085 (3) | 0.0055 (3) |
| C4 | 0.0212 (4) | 0.0155 (4) | 0.0269 (4) | −0.0007 (3) | 0.0071 (3) | −0.0001 (3) |
| C5 | 0.0194 (4) | 0.0194 (4) | 0.0185 (4) | −0.0012 (3) | 0.0046 (3) | −0.0029 (3) |
| C6 | 0.0170 (4) | 0.0181 (4) | 0.0150 (4) | −0.0011 (3) | 0.0041 (3) | 0.0006 (2) |
| C7 | 0.0184 (4) | 0.0248 (4) | 0.0181 (4) | −0.0043 (3) | 0.0066 (3) | −0.0022 (3) |
| C8 | 0.0214 (4) | 0.0285 (5) | 0.0217 (4) | 0.0005 (3) | 0.0075 (3) | 0.0031 (3) |
| C9 | 0.0198 (4) | 0.0452 (6) | 0.0282 (5) | −0.0006 (4) | 0.0078 (4) | 0.0087 (4) |
| C10 | 0.0221 (5) | 0.0601 (8) | 0.0298 (6) | −0.0150 (5) | 0.0047 (4) | −0.0037 (5) |
| C11 | 0.0326 (6) | 0.0551 (8) | 0.0434 (7) | −0.0176 (6) | 0.0098 (5) | −0.0252 (6) |
| C12 | 0.0257 (5) | 0.0374 (6) | 0.0381 (6) | −0.0072 (4) | 0.0099 (4) | −0.0189 (5) |
| C13 | 0.0293 (5) | 0.0212 (4) | 0.0226 (4) | 0.0036 (3) | 0.0080 (4) | 0.0035 (3) |
| C14 | 0.0202 (4) | 0.0263 (4) | 0.0197 (4) | −0.0038 (3) | 0.0083 (3) | −0.0015 (3) |
| O2 | 0.0197 (3) | 0.0238 (3) | 0.0282 (4) | 0.0031 (3) | 0.0110 (3) | 0.0089 (3) |
| F6 | 0.0241 (3) | 0.0285 (3) | 0.0351 (3) | 0.0055 (2) | 0.0081 (2) | 0.0144 (3) |
| F7 | 0.0196 (3) | 0.0391 (4) | 0.0381 (4) | 0.0095 (3) | 0.0078 (3) | 0.0045 (3) |
| F8 | 0.0258 (3) | 0.0483 (4) | 0.0420 (4) | −0.0016 (3) | 0.0213 (3) | 0.0024 (3) |
| F9 | 0.0418 (4) | 0.0385 (4) | 0.0417 (4) | 0.0022 (3) | 0.0251 (3) | 0.0174 (3) |
| F10 | 0.0279 (3) | 0.0272 (3) | 0.0306 (3) | 0.0099 (2) | 0.0131 (2) | 0.0118 (2) |

TABLE 4-continued

| | Antsotropic displacement parameters (Å$^2$) | | | | | |
|---|---|---|---|---|---|---|
| | $U_{11}$ | $U_{22}$ | $U_{33}$ | $U_{12}$ | $U_{13}$ | $U_{23}$ |
| C15 | 0.0186 (4) | 0.0189 (4) | 0.0180 (4) | 0.0005 (3) | 0.0061 (3) | 0.0012 (3) |
| C16 | 0.0193 (4) | 0.0208 (4) | 0.0216 (4) | 0.0015 (3) | 0.0053 (3) | 0.0027 (3) |
| C17 | 0.0178 (4) | 0.0265 (4) | 0.0242 (4) | 0.0027 (3) | 0.0055 (3) | −0.0018 (4) |
| C18 | 0.0209 (4) | 0.0306 (5) | 0.0250 (4) | −0.0020 (4) | 0.0118 (3) | −0.0020 (4) |
| C19 | 0.0274 (5) | 0.0257 (4) | 0.0229 (4) | −0.0005 (4) | 0.0126 (4) | 0.0035 (4) |
| C20 | 0.0208 (4) | 0.0216 (4) | 0.0194 (4) | 0.0031 (3) | 0.0077 (3) | 0.0030 (3) |

TABLE 5

| Selected geometric parameters (Å, °) | | | |
|---|---|---|---|
| F1—C2 | 1.3530 (11) | C10—H10 | 0.9500 |
| F2—C3 | 1.3473 (11) | C11—C12 | 1.3919 (16) |
| F3—C4 | 1.3435 (11) | C11—H11 | 0.9500 |
| F4—C5 | 1.3432 (11) | C12—H12 | 0.9500 |
| F5—C6 | 1.3489 (10) | C13—H13A | 0.9800 |
| O1—C1 | 1.3069 (11) | C13—H13B | 0.9800 |
| N1—C7 | 1.4741 (12) | C13—H13C | 0.9800 |
| N1—C14 | 1.4954 (12) | C14—H14A | 0.9800 |
| N1—C13 | 1.4993 (12) | C14—H14B | 0.9800 |
| N1—H1N | 0.928 (13) | C14—H14C | 0.9800 |
| C1—C2 | 1.4060 (12) | O2—C15 | 1.3345 (11) |
| C1—C6 | 1.4077 (12) | O2—H2O | 0.882 (16) |
| C2—C3 | 1.3825 (13) | F6—C16 | 1.3439 (11) |
| C3—C4 | 1.3809 (14) | F7—C17 | 1.3422 (11) |
| C4—C5 | 1.3810 (13) | F8—C18 | 1.3417 (11) |
| C5—C6 | 1.3810 (12) | F9—C19 | 1.3367 (12) |
| C7—C12 | 1.3826 (14) | F10—C20 | 1.3421 (11) |
| C7—C8 | 1.3831 (14) | C15—C16 | 1.3956 (13) |
| C8—C9 | 1.3966 (15) | C18—C20 | 1.3968 (13) |
| C8—H8 | 0.9500 | C16—C17 | 1.3858 (14) |
| C9—C10 | 1.381 (2) | C17—C18 | 1.3776 (15) |
| C9—H9 | 0.9500 | C18—C19 | 1.3866 (15) |
| C10—C11 | 1.386 (2) | C19—C20 | 1.3826 (14) |
| O1—C1—C2—F1 | 0.20 (13) | C7—C8—C9—C10 | 0.17 (16) |
| C6—C1—C2—F1 | 179.28 (8) | C8—C9—C10—C11 | −0.03 (19) |
| O1—C1—C2—C3 | −178.30 (9) | C9—C10—C11—C12 | −0.1 (2) |
| C6—C1—C2—C3 | 0.78 (13) | C8—C7—C12—C11 | 0.06 (19) |
| F1—C2—C3—F2 | 0.55 (14) | N1—C7—C12—C11 | −179.09 (11) |
| C1—C2—C3—F2 | 179.03 (8) | C10—C11—C12—C7 | 0.1 (2) |
| F1—C2—C3—C4 | −179.24 (8) | O2—C15—C16—F6 | 0.38 (15) |
| C1—C2—C3—C4 | −0.75 (15) | C20—C15—C16—F6 | −178.50 (9) |
| F2—C3—C4—F3 | −0.44 (14) | O2—C15—C16—C17 | 178.94 (9) |
| C2—C3—C4—F3 | 179.34 (9) | C20—C15—C16—C17 | 0.06 (14) |
| F2—C3—C4—C5 | −179.41 (9) | F6—C16—C17—F7 | 0.32 (14) |
| C2—C3—C4—C5 | 0.37 (14) | C15—C16—C17—F7 | −178.25 (9) |
| F3—C4—C5—F4 | −0.17 (14) | F6—C16—C17—C18 | 179.01 (9) |
| C3—C4—C5—F4 | 178.80 (9) | C15—C16—C17—C18 | 0.44 (15) |
| F3—C4—C5—C6 | −179.08 (9) | F7—C17—C18—F8 | −1.35 (15) |
| C3—C4—C5—C6 | −0.10 (14) | C16—C17—C18—F8 | 179.96 (9) |
| F4—C5—C6—F5 | −0.59 (13) | F7—C17—C18—C19 | 177.93 (9) |
| C4—C5—C6—F5 | 178.31 (8) | C16—C17—C18—C19 | −0.76 (15) |
| F4—C5—C6—C1 | −178.72 (8) | F8—C18—C19—F9 | 1.45 (16) |
| C4—C5—C6—C1 | 0.18 (14) | C17—C18—C19—F9 | −177.83 (10) |
| O1—C1—C6—F5 | 0.46 (13) | F8—C18—C19—C20 | 179.87 (10) |
| C2—C1—C6—F5 | −178.62 (8) | C17—C18—C19—C20 | 0.58 (15) |
| O1—C1—C6—C5 | 178.59 (9) | F9—C19—C20—F10 | −0.56 (15) |
| C2—C1—C6—C5 | −0.50 (13) | C18—C19—C20—F10 | −178.98 (9) |
| C14—N1—C7—C12 | 69.02 (12) | F9—C19—C20—C15 | 178.34 (9) |
| C13—N1—C7—C12 | −56.93 (12) | C18—C19—C20—C15 | −0.09 (16) |
| C14—N1—C7—C8 | −110.15 (10) | C16—C15—C20—F10 | −0.30 (14) |
| C13—N1—C7—C8 | 123.89 (10) | C16—C15—C20—F10 | 178.66 (9) |
| C12—C7—C8—C9 | −0.19 (16) | O2—C15—C20—C19 | −179.19 (9) |
| N1—C7—C8—C9 | 178.97 (9) | C16—C15—C20—C19 | −0.23 (14) |
| C7—N1—C14 | 111.63 (7) | C10—C11—H11 | 119.9 |
| C7—N1—C13 | 112.41 (8) | C12—C11—H11 | 119.9 |
| C14—N1—C13 | 111.35 (8) | C7—C12—C11 | 118.84 (11) |
| C7—N1—H1N | 108.5 (8) | C7—C12—H12 | 120.6 |
| C14—N1—H1N | 108.6 (8) | C11—C12—H12 | 120.6 |
| C13—N1—H1N | 104.0 (8) | N1—C13—H13A | 109.5 |
| O1—C1—C2 | 122.91 (8) | N1—C13—H13B | 109.5 |
| O1—C1—C6 | 122.82 (8) | H13A—C13—H13B | 109.5 |
| C2—C1—C6 | 114.26 (8) | N1—C13—H13C | 109.5 |

TABLE 5-continued

| Selected geometric parameters (Å, °) | | | |
|---|---|---|---|
| F1—C2—C3 | 118.78 (8) | H13A—C13—H13C | 109.5 |
| F1—C2—C1 | 117.92 (8) | H13B—C13—H13C | 109.5 |
| C3—C2—C1 | 123.28 (9) | N1—C14—H14A | 109.5 |
| F2—C3—C4 | 119.78 (9) | N1—C14—H14B | 109.5 |
| F2—C3—C2 | 120.03 (9) | H14A—C14—H14B | 109.5 |
| C4—C3—C2 | 120.19 (8) | N1—C14—H14C | 109.5 |
| F3—C4—C3 | 121.05 (9) | H14A—C14—H14C | 109.5 |
| F3—C4—C5 | 120.18 (9) | H14B—C14—H14C | 109.5 |
| C3—C4—C5 | 118.77 (8) | C15—O2—H2O | 115.5 (10) |
| F4—C5—C4 | 119.65 (8) | O2—C15—C16 | 125.46 (8) |
| F4—C5—C6 | 119.86 (8) | O2—C15—C20 | 118.80 (8) |
| C4—C5—C6 | 120.48 (8) | C16—C15—C20 | 115.93 (8) |
| F5—C6—C5 | 118.35 (8) | F6—C16—C17 | 118.53 (8) |
| F5—C6—C1 | 118.61 (8) | F6—C16—C15 | 119.45 (8) |
| C5—C6—C1 | 123.02 (8) | C17—C16—C15 | 122.01 (9) |
| C12—C7—C8 | 121.88 (9) | F7—C17—C18 | 119.81 (9) |
| C12—C7—N1 | 119.48 (9) | F7—C17—C16 | 119.54 (9) |
| C8—C7—N1 | 118.63 (8) | C18—C17—C16 | 120.63 (9) |
| C7—C8—C9 | 118.69 (10) | F8—C18—C17 | 120.63 (9) |
| C7—C8—H8 | 120.7 | F8—C18—C19 | 120.37 (10) |
| C9—C8—H8 | 120.7 | C17—C18—C19 | 118.79 (9) |
| C10—C9—C8 | 120.23 (11) | F9—C19—C20 | 119.57 (9) |
| C10—C9—H9 | 119.9 | F9—C19—C18 | 120.31 (9) |
| C8—C9—H9 | 119.9 | C20—C19—C18 | 120.10 (9) |
| C9—C10—C11 | 120.35 (10) | F10—C20—C19 | 118.36 (8) |
| C9—C10—H10 | 119.8 | F10—C20—C15 | 119.10 (8) |
| C11—C10—H10 | 119.8 | C19—C20—C15 | 122.53 (9) |
| C10—C11—C12 | 120.10 (12) | | |

What is claimed is:

1. An ionic compound of the formula:

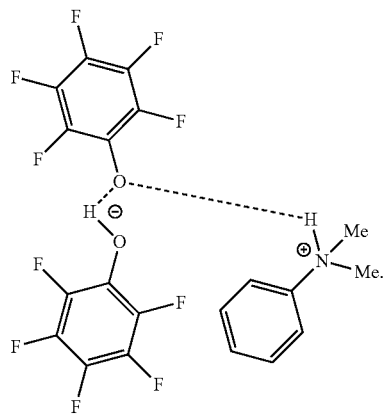

2. A compound derived from at least N,N-dimethylaniline and pentafluorphenol in amounts such that there are at least two equivalents of pentafluorophenol per equivalent of the N,N-dimethylaniline.

3. A method of making the ionic compound of claim 1, comprising combining at least N,N-dimethylaniline and pentafluorphenol in amounts such that there are at least two equivalents of pentafluorophenol per equivalent of the N,N-dimethylaniline.

* * * * *